US009757022B2

(12) United States Patent
Mankowski et al.

(10) Patent No.: US 9,757,022 B2
(45) Date of Patent: Sep. 12, 2017

(54) AUTOMATED METHODS TO COUNT CORNEAL SUBBASAL NERVES

(71) Applicants: THE JOHNS HOPKINS UNIVERSITY, Baltimore, MD (US); VOXELERON LLC, Pleasanton, CA (US)

(72) Inventors: Joseph L. Mankowski, Severna Park, MD (US); Jonathan D. Oakley, Pleasanton, CA (US); Daniel B. Russakoff, San Francisco, CA (US)

(73) Assignees: THE JOHNS HOPKINS UNIVERSITY, Baltimore, MD (US); VOXELERON, LLC, Pleasanton, CA (US)

( * ) Notice: Subject to any disclaimer, the term of this patent is extended or adjusted under 35 U.S.C. 154(b) by 0 days.

(21) Appl. No.: 15/152,645

(22) Filed: May 12, 2016

(65) Prior Publication Data

US 2016/0331225 A1 Nov. 17, 2016

Related U.S. Application Data

(60) Provisional application No. 62/160,158, filed on May 12, 2015, provisional application No. 62/169,625, filed on Jun. 2, 2015.

(51) Int. Cl.
*A61B 3/10* (2006.01)
*A61B 3/00* (2006.01)
*A61B 3/13* (2006.01)
*A61B 5/00* (2006.01)

(52) U.S. Cl.
CPC .......... *A61B 3/0025* (2013.01); *A61B 3/1025* (2013.01); *A61B 3/13* (2013.01); *A61B 5/4047* (2013.01); *A61B 5/0068* (2013.01); *A61B 5/4029* (2013.01); *A61B 2576/02* (2013.01)

(58) Field of Classification Search
USPC .................................................. 351/200–246
See application file for complete search history.

(56) References Cited

U.S. PATENT DOCUMENTS 8,801,187 B1 * 8/2014 Knighton ............... A61B 3/102
345/418
9,101,293 B2 * 8/2015 Everett .................. A61B 3/102

* cited by examiner

*Primary Examiner* — Mohammed Hasan
(74) *Attorney, Agent, or Firm* — Johns Hopkins Technology Ventures

(57) ABSTRACT

The present invention is directed to a software algorithm that measures the number of corneal nerve fibers in images captured by microscopy including images from patients obtained by in vivo corneal confocal microscopy, a noninvasive technique. The present invention solves a complicated segmentation problem, by exploiting the piece wise linear nature of the nerve fibers—i.e., the nerves are made up of a lot of straight line segments. The image is split into sub-regions, where each sub-region contains nerves mostly running in the same, straight direction. Having the nerves all in straight-lines within a single 2d image region dramatically simplifies the segmentation problem. The image intensities are summed in the direction of the nerves to reduce the 2d representation to a 1d signal having pronounced peaks where the nerves are located.

20 Claims, 6 Drawing Sheets

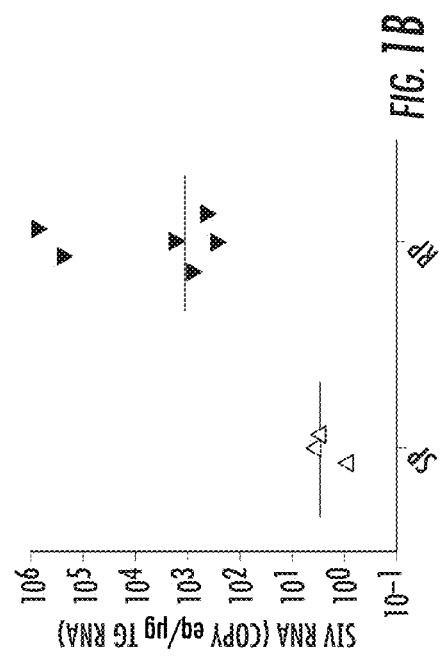
FIG. 1A
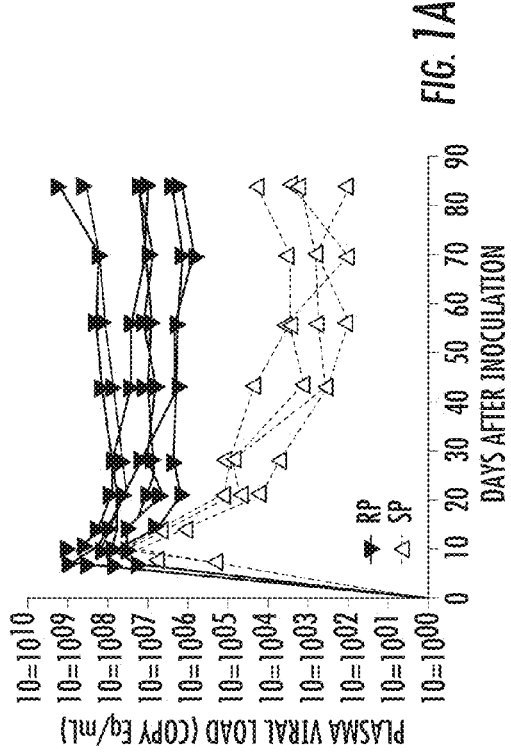
FIG. 1C
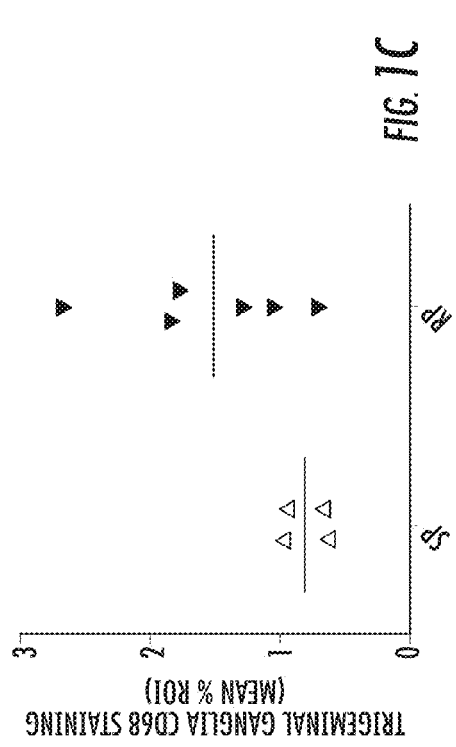
FIG. 1B
FIG. 1D

AUTOMATED METHODS TO COUNT CORNEAL SUBBASAL NERVES

CROSS REFERENCE TO RELATED APPLICATIONS

This application claims the benefit of U.S. Provisional Patent Application No. 62/160,158 filed May 12, 2015 and U.S. Provisional Patent Application No. 62/169,625 filed Jun. 2, 2015, which are incorporated by reference herein, in their entirety.

GOVERNMENT SUPPORT

This invention was made with government support under R01 NS055651, awarded by the National Institutes of Health. The government has certain rights in the invention.

FIELD OF THE INVENTION

The present invention relates generally to medical devices. More particularly the present invention relates to automated methods to count corneal subbasal nerves.

BACKGROUND OF THE INVENTION

Peripheral neuropathy is the most frequent neurological complication of HIV infection, affecting more than one-third of infected patients, including patients treated with antiretroviral therapy. Although emerging noninvasive techniques for corneal nerve assessments are increasingly being used to diagnose and monitor peripheral neuropathies, corneal nerve alterations have not been characterized in HIV.

Peripheral neuropathy (PN) is the most frequent neurological complication caused by HIV-1, affecting more than one-third of infected persons, including patients receiving combination antiretroviral therapy. The typical clinical presentation is known as distal sensory polyneuropathy, a length-dependent neuropathy that is characterized by bilateral aching, painful numbness or burning, and is most pronounced in the lower extremities. Although HIV-induced PN (HIV-PN) is not life threatening, this debilitating disorder greatly compromises patient quality of life. Currently, skin biopsy is the accepted standard for measuring the loss of small, unmyelinated C fibers in the epidermis, one of the earliest detectable signs of damage to the peripheral nervous system (PNS). However, skin biopsy is an invasive procedure, and longitudinal assessment requires repeated surgical biopsies. Electrophysiological testing to measure properties of peripheral nerve conduction is not considered a viable alternative because current methods lack the sensitivity required to detect damage to small, unmyelinated fibers, especially in early stages of disease. For these reasons, new, sensitive, noninvasive methods of assessing small fiber nerve damage are urgently needed to detect and monitor PN in persons infected with HIV.

Like HIV, small sensory nerve fiber loss is common in patients with diabetes mellitus and results in a clinical syndrome that closely resembles HIV distal sensory polyneuropathy. Of interest, studies have documented the utility of measuring changes in corneal sensory innervation to track diabetic neuropathy as an alternative to measuring epidermal nerve fiber (ENF) density via skin biopsy. In particular, decreases in the nerve density in the corneal subbasal plexus (SBP) have been reported in both isolated corneal whole mount studies and by noninvasive in vivo corneal confocal microscopy (CCM). The use of corneal alterations in tracking HIV-induced neuropathy has yet to be explored.

It would therefore be advantageous to provide a fast, accurate, and non-invasive method for counting corneal nerve fibers.

SUMMARY

According to a first aspect of the present invention a non-transitory computer readable medium programmed with steps including receiving image data related to a region of interest of the subject. The steps include dividing the image data into sub-regions. Each sub-region is defined by selecting for nerve fibers running in approximately a same direction. The steps also include summing image intensities in the same direction of the nerve fibers for the sub-region to reduce a two-dimensional representation to a one-dimensional signal having peaks where the nerve fibers are located. Additionally, the steps include determining a nerve fiber count based on counting the peaks of the one-dimensional signal.

In accordance with an aspect of the present invention, the non-transitory computer readable medium further executes a step of receiving image data related to a cornea of the subject. The non-transitory computer readable medium receives image data from in vivo corneal confocal microscopy. The non-transitory computer readable medium receives image data from a whole mount specimen. The whole mount specimen can be immunostained for the pan-axonal marker βIII tubulin. The non-transitory computer readable medium is further configured for comparing the nerve fiber count to a previous nerve fiber count or a normal nerve fiber count to diagnose peripheral neuropathy and comparing the nerve fiber count to a previous nerve fiber count in order to diagnose changes in peripheral neuropathy within the individual subject. The non-transitory computer readable medium can receive in vivo image data from a confocal microscope. The non-transitory computer readable medium is programmed for deriving measures of length, tortuosity, branching, and density to diagnose peripheral neuropathy.

In accordance with another aspect of the present invention, a system for diagnosing peripheral neuropathy in a subject includes a confocal microscope configured for obtaining image data of a region of interest of a cornea of the subject. The system includes a non-transitory computer readable medium. The non-transitory computer readable medium is programmed for receiving the image data of the region of interest of the cornea of the subject. The non-transitory computer readable medium is programmed for dividing the image data into sub-regions. Each sub-region is defined by having nerve fibers running in approximately a same direction. Further, the non-transitory computer readable medium is programmed for summing image intensities in the same direction of the nerve fibers for the sub-region and reducing a two-dimensional representation to a one-dimensional signal having peaks where the nerve fibers are located. Additionally, the non-transitory computer readable medium is programmed for determining a nerve fiber count based on the peaks of the one-dimensional signal.

In accordance with yet another aspect of the present invention, the non-transitory computer readable medium is programmed for comparing the nerve fiber count to a previous nerve fiber count or a normal nerve fiber count to diagnose peripheral neuropathy. The nerve fiber count is compared to a previous nerve fiber count in order to diagnose onset of or changes in extent of peripheral neuropathy.

In vivo image data is received from a confocal microscope. Measures of length, tortuosity, branching, and density to diagnose peripheral neuropathy are derived from the image data. The system includes a computing device. The computing device is networked with the confocal microscope in order to receive the image data. A database is included for storing the image data. A computing device is networked with the database for receiving the image data. Image data stored on the data base is analyzed to determine baseline never counts that indicate peripheral neuropathy. Peripheral neuropathy is assessed based on the nerve fiber count.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIGS. 1A-1D illustrate graphical views of SIV plasma viral load (PVL) over time and SIV-induced alterations in SIV RNA, CD68, and GFAP expressions in trigeminal ganglia according to severity of SIV infection. FIG. 1A illustrates a graphical view of longitudinal plasma SIV RNA levels, which depict a markedly lower viral set point among the singly inoculated macaques, classified as SPs, than do the dual-inoculated macaques that sustained high plasma viremia and progressed to AIDS, classified as RPs. FIG. 1B illustrates a scatter plot depicting the SIV viral load in the TG indicates increased SIV replication in the TG of RPs compared with SPs. FIG. 1C illustrates CD68 immunostaining of the TG indicates a marked increase in macrophage activation and infiltration in the TG among the RPs, concomitant with the increased severity of SIV infection. FIG. 1D illustrates GFAP immunostaining of glial satellite cells in the TG was similarly significantly increased among the RPs. Horizontal lines represent median values. P=0.024 (FIG. 1B) and P=0.0095 (FIG. 1D), both by Mann-Whitney test. ROI, region of interest; RP, rapid progressor; SP, slow progressor; TG, trigeminal ganglion.

FIG. 2A illustrates an image of the corneal SBP of 5 mm corneal whole mount immunostained for the neuronal marker βIII tubulin shows the dense sensory nerve fibers throughout the cornea. FIGS. 2B and 2C illustrate representative images of the SBP among slow progressors show dense, regularly spaced nerve fibers. FIGS. 2D and 2E illustrate images of the SBP from the rapid progressors exhibit lower CNF density than the slow progressors. For image comparison, black and white images were pseudocolored to green and black with the use of iVision software. Scale bar=100 µmol/L. Original magnifications: ×20 (FIG. 2A); ×200 (FIGS. 2B-2E).

FIG. 3A illustrates an image of the SBP of an RP animal represents the βIII tubulin immunostained images acquired for both the manual and automated quantitative assessment of CNF. FIG. 3B illustrates that for manual quantitative assessment, transects (blue lines) were drawn perpendicular to the longitudinal nerve trunks and nerve fibers crossing each transect (denoted by red circles) were counted. The number of nerve fibers counted was then divided by the length of each transect, and the average number of nerves per millimeter was calculated. FIG. 3C illustrates that the automated method used a custom algorithm (Voxeleron) to identify and then quantify CNFs. Applying filters generated an output image that depicted which nerve fibers would be detected by the algorithm. FIG. 3D illustrates that the automated algorithm used a series of steps to count nerve fibers. Each ×200 image was first subdivided into 16 smaller images that were then rotated to achieve a vertical orientation (top panel). The image pixel data were then summed along the vertical axis (middle panel), generating a 1D profile in which each peak represented a single nerve fiber denoted by an asterisk at the top of counted nerve fibers (bottom panel). Lower peaks that did not correspond to a nerve fiber were excluded by thresholding. FIG. 3E illustrates a graphical view of a strong positive correlation was found between the two counting methods. FIG. 3F illustrates a graphical view of a statistically significant decrease in CNFs among the RP group versus the SP group was found by using the automated method of quantitative assessment. FIG. 3G illustrates a graphical view that the manual method of quantitative assessment also found a statistically significant decrease in CNFs among the RPs. Lines represent median values (FIGS. 3E-3G). P=0.0061 and P=0.024 (FIG. 3G), both by Mann-Whitney test; and P=0.0004, r=0.90, Spearman rank correlation (FIG. 3G). Original magnification ×200 (FIGS. 3A-3C). RP, rapid progressors; SP, slow progressors.

FIG. 4A illustrates a significant, direct correlation is observed between ENF length and CNF density by using the manual method of quantitative assessment. FIG. 4B illustrates the automated method of CNF quantitative assessment also shows a significant, direct correlation between CNF and ENF length, indicating the potential of CNF assessment as a surrogate measure in the evaluation of HIV-PN. Lines represent median values. P=0.048, r=0.62 (FIG. 4A) and P=0.040, r=0.64 (FIG. 4B), both Spearman rank correlation.

DETAILED DESCRIPTION OF THE PREFERRED EMBODIMENTS

Figure 2A:
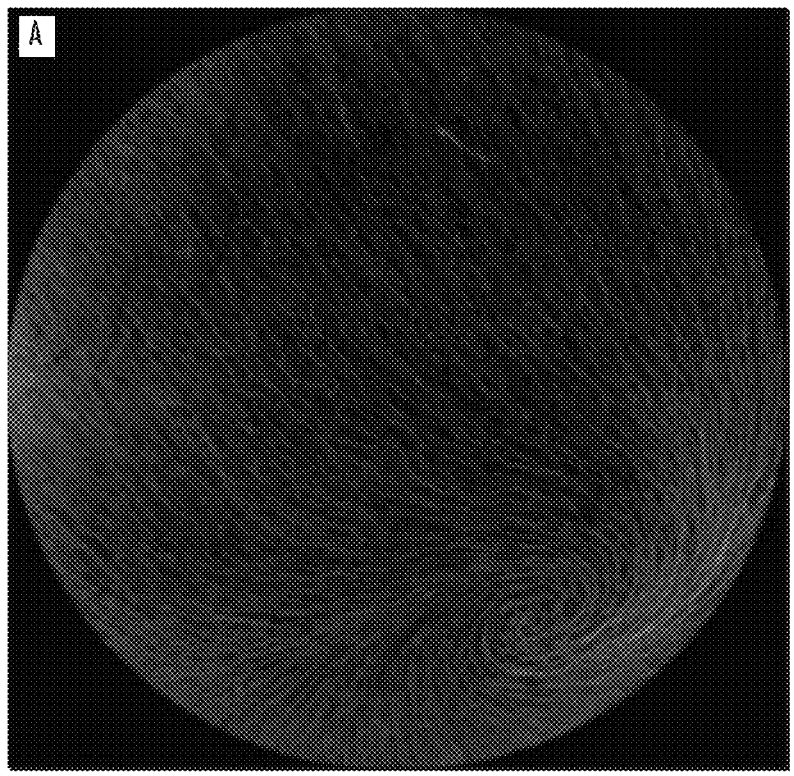
FIGS. 2A-2E illustrate images of representative βIII tubulin immunostaining of corneal SBP nerve fibers in rapid progressors compared with slow progressors.
Figure 2B:
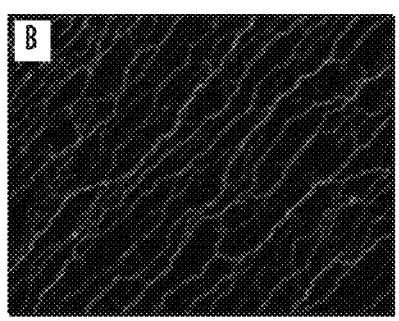
Figure 2C:
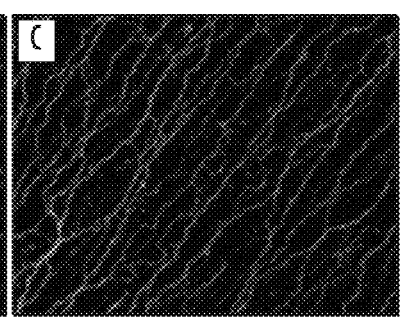
Figure 2D:
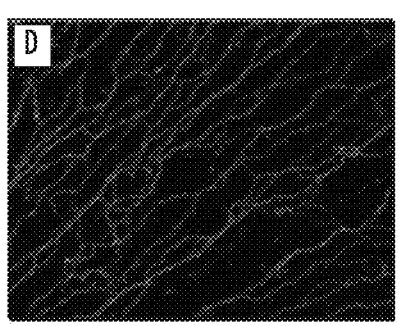
Figure 2E:
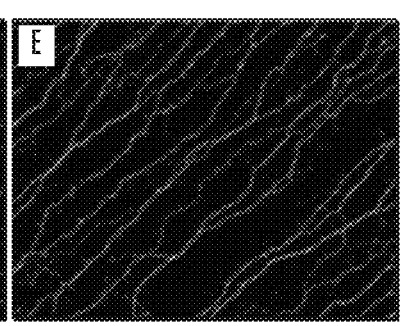

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a software algorithm that measures the number of corneal nerve fibers in images captured by microscopy including images from patients obtained by in vivo corneal confocal microscopy, a noninvasive technique. The present invention solves a complicated segmentation problem that exploits the piece-wise linear nature of the nerve fibers—i.e., the nerves are made up of a lot of straight line segments. The image is automatically split into sub-regions, such that each sub-region contains nerves mostly running in the same, straight direction. Having the nerves arranged all in straight-lines within a single 2d image region dramatically simplifies the segmentation problem. The image intensities are summed in the direction of the nerves to reduce the 2d representation to a 1d signal having pronounced peaks where the nerves are located.

Although emerging non-invasive techniques for corneal nerve assessments are increasingly being utilized to diagnose and monitor peripheral neuropathies, robust automated methods to measure nerves in the corneal subbasal plexus have not been developed. To automate nerve counts in the cornea, the present invention includes a custom algorithm to quantify nerve fibers in corneal subbasal plexus images in whole mount specimens immunostained for the pan-axonal marker βIII tubulin. This novel counting method is applicable to corneal whole mounts and for images obtained in patients by in vivo corneal confocal microscopy. Equally, the method of the present invention translates directly to clinical application, as it has been successfully applied to the HRT Rostock confocal microscope (Heidelberg Engineering, Heidelberg, Germany).

The present invention is advantageous over other techniques based on its simplicity and effectiveness. Other methods are all based on edge detection techniques using complex filter banks and iterative segmentation methods that attempt to, at each pixel, separate edges from background. In noisy data, high frequency noise and edges are often difficult to separate. The results of the present invention are less susceptible to noise in the image data as the information is averaged out, and as long as the piece-wise linear assumption holds, a more robust metric for nerve fiber count and density is created.

In an exemplary implementation of the present invention, which is no way to be considered limiting, to determine whether SIV infection leads to corneal nerve fiber loss, corneas were immunostained for the nerve fiber marker βIII tubulin. Both manual and automated methods were applied to measure nerves in the corneal subbasal plexus. These counting methods independently indicated significantly lower subbasal corneal nerve fiber density among SIV-infected animals that rapidly progressed to AIDS compared with slow progressors. Concomitant with decreased corneal nerve fiber density, rapid progressors had increased levels of SIV RNA and CD68-positive macrophages and expression of glial fibrillary acidic protein by glial satellite cells in the trigeminal ganglia, the location of the neuronal cell bodies of corneal sensory nerve fibers. In addition, corneal nerve fiber density was directly correlated with epidermal nerve fiber length. These findings indicate that corneal nerve assessment has great potential to diagnose and monitor HIV-induced peripheral neuropathy and to set the stage for introducing noninvasive techniques to measure corneal nerve fiber density in HIV clinical settings.

To study the pathogenesis of HIV-induced PNS disease, a SIV-infected macaque model was developed that closely recapitulates key PNS alterations seen in patients with HIV with PN. These changes include macrophage infiltration, SIV replication, and neuronal loss in sensory ganglia, including the trigeminal ganglia, which house the cell bodies of sensory neurons that innervate the cornea. In this exemplary embodiment, a goal was to determine whether SIV infection leads to decreases in corneal nerve fiber (CNF) density, whether changes in corneal nerves correspond with the extent of SIV replication and the severity of cellular immune responses in the trigeminal ganglia, and whether CNF density correlates with ENF length, thereby setting the stage for follow-up CCM investigation. To achieve optimal immunostaining of the corneal SBP, an immunohistochemical staining method was modified. Because conventional image analysis of the corneal nerve is labor intensive and requires trained observers, two novel counting methods were used: a relatively simple manual counting method of nerve fibers and an automated method of nerve detection and counting to facilitate efficient, objective assessment of nerve fiber density, which represents the present invention.

Male juvenile pigtailed macaques (*Macaca nemestrina*) were inoculated intravenously with either a combination of the infectious clone SIV/17E-Fr and the viral swarm SIV/DeltaB670 (n=7) or with the infectious clone SIV/17E-Fr (n=4). Serology was negative for SIV, simian T-cell leukemia virus, and simian type D retrovirus for all macaques before inoculation. For control purposes, corneas also were obtained from three additional uninfected macaques. Animals were housed in Johns Hopkins University facilities that are fully accredited by the Association for Assessment and Accreditation of Laboratory Animal Care International. Macaques were fed a commercial macaque diet (Harlan, Indianapolis, Ind.), given water ad libitum, and provided with environmental enrichment daily. All procedures were approved by the Johns Hopkins University Institutional Animal Care and Use Committee and were conducted in accordance with guidelines set forth in the Animal Welfare Regulations (US Department of Agriculture) and the Guide for the Care and Use of Laboratory Animals (Office of Laboratory Animal Welfare).

To evaluate SIV RNA levels, RNA was extracted from frozen trigeminal ganglia or plasma. Viral load was measured by quantitative RT-PCR with the use of primers to quantitate SIV gag.

After euthanasia, an 8-mm biopsy punch was used to remove the central cornea from the eye. Corneas were immediately placed in 0.1 mol/L PBS and stored at 4° C. for 8 hours before preservation in 10% neutral-buffered formalin. Corneas were then fixed overnight at 4° C., rinsed three times in PBS, and cryoprotected overnight at 4° C. in 20% glycerol/0.1 mol/L Sørensen's phosphate buffer. Before immunostaining, a 5-mm biopsy punch was used to remove the central corneal button, which was then immunostained as a free-floating whole mount. To enhance permeability, whole mounts were incubated for 48 hours at 37° C. in 0.01% hyaluronidase (type IV-S; Sigma-Aldrich, St. Louis, Mo.) and 0.1% EDTA (Sigma-Aldrich) in 0.1 mol/L PBS (pH 5.3). Corneal buttons were then washed three times for 15 minutes each in PBS that contained 0.3% Triton X-100 and also between each subsequent immunostaining step. Nonspecific labeling was blocked by incubation at room temperature for 2 hours in blocking serum (1% bovine serum albumin in PBS that contained 0.3% Triton X-100) before a 4-day incubation at room temperature with a mouse monoclonal antibody against the neuronal marker βIII tubulin (1:500; Promega Corporation, Madison, Wis.). Corneal buttons were then incubated in secondary antibody (biotinylated goat anti-mouse IgG, 1:200; Vector Laboratories, Burlingame, Calif.) followed by avidin-biotin-horseradish peroxidase complex (Vectastain Elite ABC Reagent; Vector Laboratories) for 2 hours each at room temperature and subsequent detection with the diaminobenzidine chromogen (Sigma-Aldrich) after incubation for 10 to 15 minutes. After washing, corneas were mounted on chrome alum-gelatin-coated slides and air-dried overnight. Tissue slides were then washed in distilled water, dehydrated in graded alcohols, cleared in HistoClear (National Diagnostics, Atlanta, Ga.), and coverslipped with Permount (Fisher Scientific, Pittsburgh, Pa.).

For each cornea, images of five ×200 fields (one field from each quadrant and one field from the central cornea) of the SBP were captured with a Retiga 2000R digital camera (QImaging, Surrey, BC, Canada) mounted on a Nikon E600 microscope (Nikon, Tokyo, Japan). Several serial Z-stack images were taken of each field to accommodate for the curvature of the cornea, thus bringing the entire SBP of the field into a single focused plane. The subregions of SBP in focus for each image were selected in Adobe Photoshop CS4 software version 11.0 (Adobe Systems, San Jose, Calif.) and autoblended to assemble a single cohesive image of the subbasal nerve plexus for each field. The blended images were subsequently used in the quantitative assessment of nerve fiber density.

Corneal SBP nerves were counted with Stereo Investigator software version 9 (MicroBrightField Inc, Colchester, Vt.) to draw three transect lines across each image oriented perpendicular to the longitudinal subbasal nerve fibers. The number of nerves crossing each transect was counted and then divided by the total transect length. For each image, the number of nerves crossing each of the three transects was averaged, and the final mean number of corneal nerves per millimeter was derived from the five images for each animal.

To automate nerve counts in the cornea, a custom algorithm was developed specifically to quantify nerve fibers in SBP images to emulate the manual counting method. The reduction to practice of the automated algorithm includes the following steps. First, anisotropic diffusion filtering was applied to reduce noise while preserving the structure of each image. The linear structure of the nerves was then enhanced across various scales with the use of Frangi's Hessian-based filter. To exploit the piecewise linearity of the nerves, the image was automatically subdivided into smaller regions based on a measure of directional linearity in each of the subregions. As such, the size of each subregion is a parameter determined based on measures of how directional the fibers in each subregion are. Taken as a whole, this could include principal component analysis to estimate orientation of the data in a given direction, where the ratio of the principal direction to the next orthogonal direction indicate well this distribution. In determining subregions of the image in which nerves exhibited the same orientation, the resulting reorientation further refines (ie, most prominent) orientation of the nerves; in this reduction to practice, it is defined as minimal entropy of the distribution of image data in the resulting 1D profile. The number of visible nerves was determined by summing image data along the most prominent orientation and then counting the peaks in the 1D profile, with each peak representing a single nerve fiber. The nerve count was derived cumulatively from the sum of the peaks per image for each of the five images.

IHC was performed on HistoChoice-fixed (HistoChoice Tissue Fixative; Amresco, Solon, Ohio) paraffin-embedded sections of trigeminal ganglia. Tissue sections were deparaffinized by heating for 30 minutes at 60° C., cleared in changes of HistoClear (National Diagnostics), and then rehydrated in a graded series of alcohol. Slides were pretreated for antigen retrieval by heating with 0.01 mol/L sodium citrate (pH 6.0) before immunostaining. Endogenous peroxidases were blocked with 3% hydrogen peroxide in methanol, then nonspecific labeling was blocked with dilute block (Vector Laboratories). Sections were incubated in the appropriate primary antibody dilution [CD68, 1:4000, clone KP1, and glial fibrillary acidic protein (GFAP), 1:80, 000; Dako, Carpinteria, Calif.] for 1 hour, followed by biotinylated anti-mouse/rabbit secondary antibody and avidin-biotin-horseradish peroxidase complex (Vectastain Elite ABC Reagent; Vector Laboratories) for 30 minutes each with subsequent detection with the diaminobenzidine chromogen (Vector Laboratories). Tissue sections were then washed, cleared, and coverslipped with Permount (Fisher Scientific). The amount of immunostaining for the macrophage marker CD68 and satellite cell marker GFAP was measured by digitized image analysis as described. For each trigeminal ganglion, 20 nonoverlapping fields at ×200 magnification were captured with a Retiga 2000R digital camera (QImaging) mounted on a Nikon E600 microscope (Nikon). Binarized images were then analyzed with iVision imaging software version 4.0.14 (BioVision Technologies, Exton, Pa.). The mean total area occupied by the immunopositive pixels in the trigeminal ganglion was calculated for each animal.

To measure ENF density in the skin of the plantar footpad surface of the hind limb, 3-mm diameter punch footpad samples were obtained at necropsy from the identical site. Footpad skin sections were fixed for 12 to 24 hours in 2% paraformaldehyde/lysine/periodate fixative at 4° C., rinsed with 0.08 mol/L Sorensen's phosphate buffer, and then transferred to cryoprotective buffer (20% glycerol in 0.08 mol/L Sørensen's phosphate buffer) until processed as previously described. Cryoprotected samples were sectioned at a thickness of 50 µm on a sliding microtome and then immunostained for PGP9.5, a pan axonal marker (1:2000; Chemicon, Temecula, Calif.), as previously described.

PGP9.5 ENF length was quantified with unbiased stereology methodology by using the space ball probe on Stereo Investigator software version 9 (MBF Bioscience, Williston, Vt.). Three 50-µm PGP9.5 immunostained sections from one plantar footpad biopsy from each animal were measured. The area of interest was defined as the epidermal region that extended from the epidermal/dermal junction to the stratum corneum and was drawn under a Nikon 4×/0.2 Plan Apo objective on a Nikon Eclipse E600 light microscope. The ENF length was measured with a Nikon 60×/1.40 oil Plan Apo objective. The radius of the hemisphere probe was 30 µm with a guard zone of 2 µm. Only nerve fibers within the epidermis were counted. The results were expressed as the length of PGP9.5 nerve fibers. All stereology measurements were obtained with DAT files of Stereo Investigator.

Seven animals were dual-inoculated with SIV/17E-Fr, an infectious clone, and with SIV/DeltaB670, an immunosuppressive swarm. An additional four animals were inoculated with only the molecular clone SIV/17E-Fr. To track SIV disease progression, plasma viral loads (PVLs) were measured by quantitative RT-PCR in longitudinal samples obtained from acute through terminal disease time points. During acute infection, all animals developed similar high PVLs with peak SIV RNA levels at 10 to 14 days after inoculation of $10^7$ to $10^9$ RNA copies/mL (FIG. 1A). Among the dual-inoculated animals, the viral set point remained high, and at the time of sacrifice (84 days after inoculation), dual-inoculated animals had progressed to AIDS with severely diminished $CD4^+$ T-lymphocyte counts (median terminal PVL=$1.18 \times 10^7$ copies/mL, median terminal $CD4^+$ T cells/µL=276). In contrast, the singly inoculated animals had a much lower PVL set point after acute infection that continued to the time of sacrifice (median terminal PVL=$1.89 \times 10^3$ copies/mL) and also maintained a significantly higher $CD4^+$ T-lymphocyte count (median terminal $CD4^+$ T cells/µL=989; P=0.0061) than did the dual-inoculated macaques. Given these differences between groups, dual-inoculated versus singly inoculated animals were classified as rapid progressors and slow progressors, respectively, in subsequent group comparisons.

Figure 3A:
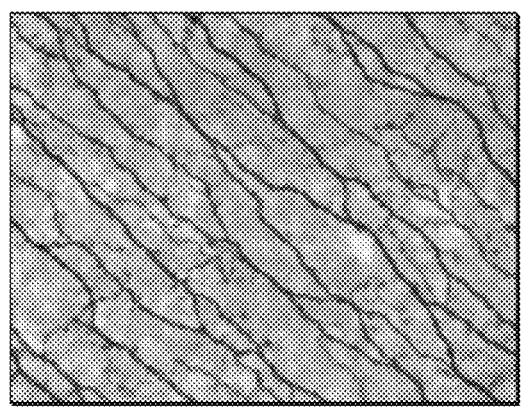
FIGS. 3A-3G illustrate image and graphical views of manual and automated methods to measure CNF counts in RP compared with SP SIV-infected macaques.
Figure 3B:
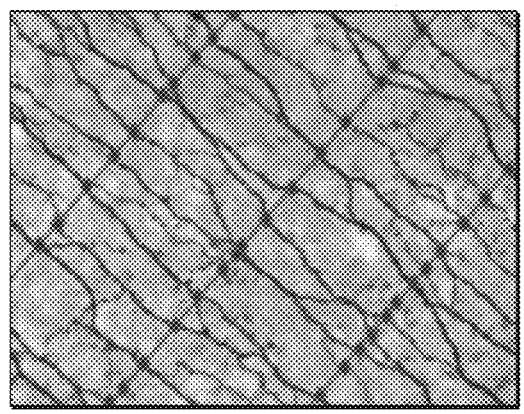
Figure 3C:
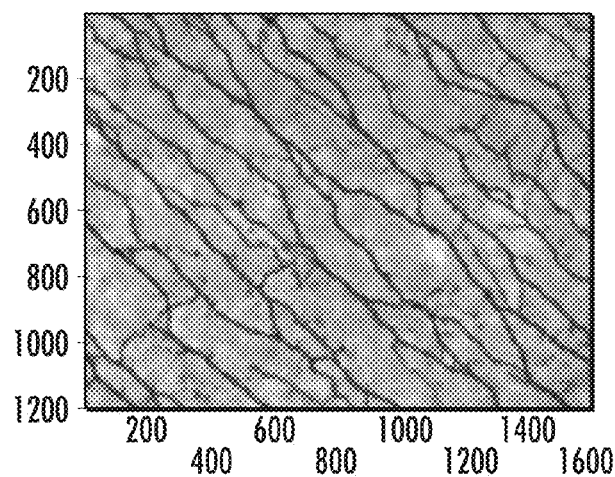
Figure 3D:
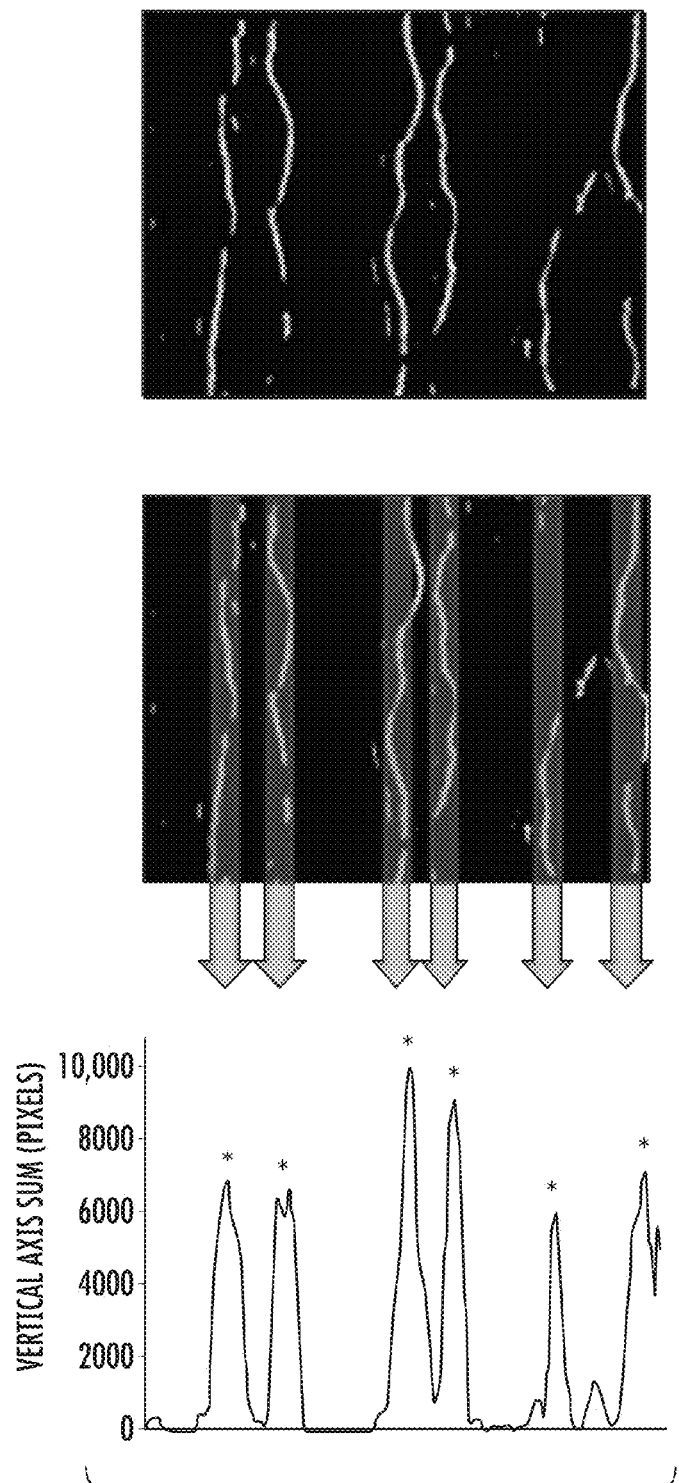
Figure 3E:
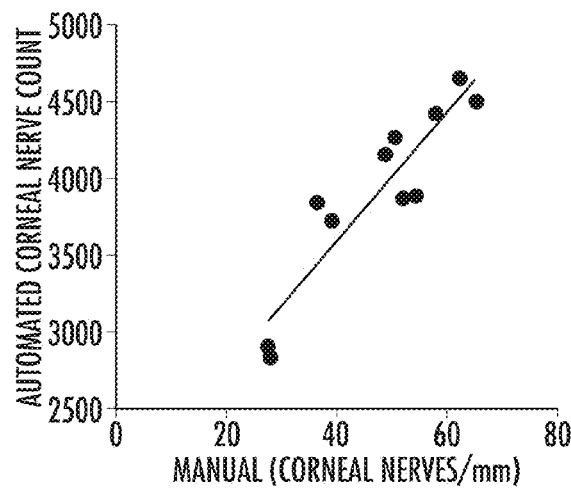
Figure 3F:
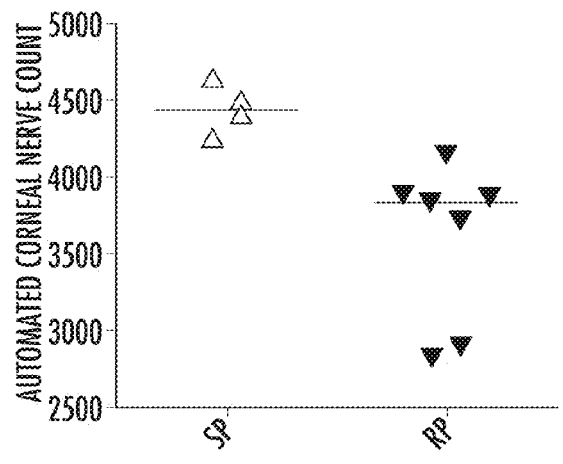
Figure 3G:
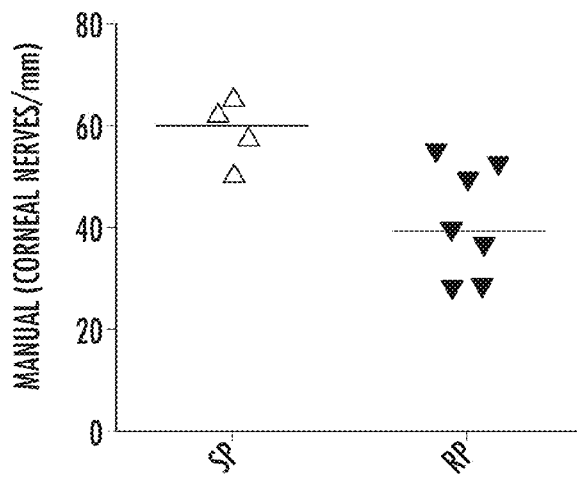

To determine whether SIV infection induced nerve fiber loss in the corneal SBP, cornea whole mounts 5 mm in diameter were immunostained for the neuronal marker βIII tubulin (FIG. 2A). Visual inspection of these images indicated lower nerve fiber density in the rapid progressor group than in the slow progressor group (FIGS. 2B-2E). To measure the number of CNFs, identical ×200 images of the SBP were analyzed both by counting manually and by an automated counting method (FIGS. 3A-3D). Manual and automated CNF counts showed a strong, positive correlation between nerve fiber counts (P=0.0004, r=0.90), indicating excellent agreement between the two counting methods (FIG. 3E). Both counting methods showed a significantly decreased CNF count among the rapid progressors than among the slow progressors; the decline was more robust by using the automated detection algorithm (P=0.024 for manual counts; P=0.0061 for automated counts) (FIGS. 3F and 3G). CNF loss was uniform across sample fields in individual animals. Neither manual nor automated CNF counts from uninfected control animals were significantly different from corneal nerve counts measured in slow progressors (P>0.05). This was an expected finding, given that approximately 50% of persons infected with HIV do not have evidence of PNS damage.

Previous studies have shown SIV replication in the sensory ganglia of dual-inoculated SIV-infected macaques at terminal end points. To investigate whether SIV replication in the trigeminal ganglia differed between progressor groups, SIV RNA levels were measured by quantitative RT-PCR. SIV RNA in the trigeminal ganglia among the rapid progressors was significantly elevated (median SIV RNA=1076 copies/μg RNA; P=0.024) (FIG. 1B) compared with the slow progressors with low to undetectable SIV RNA levels (median SIV RNA=3 copies/μg RNA).

In the sensory ganglia of macaques, key cellular immune responders, including macrophages and satellite cells, are activated in response to SIV infection. To determine whether there were differences in cellular immune responses between the rapid progressor and slow progressor groups, trigeminal ganglia sections were stained separately for the macrophage marker CD68 and the satellite cell marker GFAP. The amount of CD68 and GFAP immunostaining was then measured by quantitative image analysis. Immunostaining for both CD68-positive macrophages and GFAP-expressing satellite cells was higher in the rapid progressor group than in the slow progressor group (P=0.054 and P=0.0095, respectively) (FIGS. 1C and 1D). Furthermore, both macrophage (CD68 immunostaining: P=0.014, r=0.80) and satellite cell activation (GFAP immunostaining: P=0.0031, r=0.88) were strongly correlated with SIV RNA levels in the trigeminal ganglia, thus indicating a positive relationship between the extent of productive SIV infection and corresponding severity of inflammation in the sensory ganglia.

The CNF count measured by the automated algorithm was inversely correlated with terminal PVL (P=0.040, r=−0.64), indicating a relationship between the extent of productive SIV infection and corneal nerve damage. CNF density was also related to both the extent of SIV replication (P=0.067, r=−0.65) and macrophage activation in the trigeminal ganglia (P=0.067, r=−0.61), but the small group sizes in the study did not allow us to uncover definitive relationships. In contrast, satellite cell activation in the trigeminal ganglia was not associated with CNF count (P=0.10, r=−0.55).

Figure 4B:
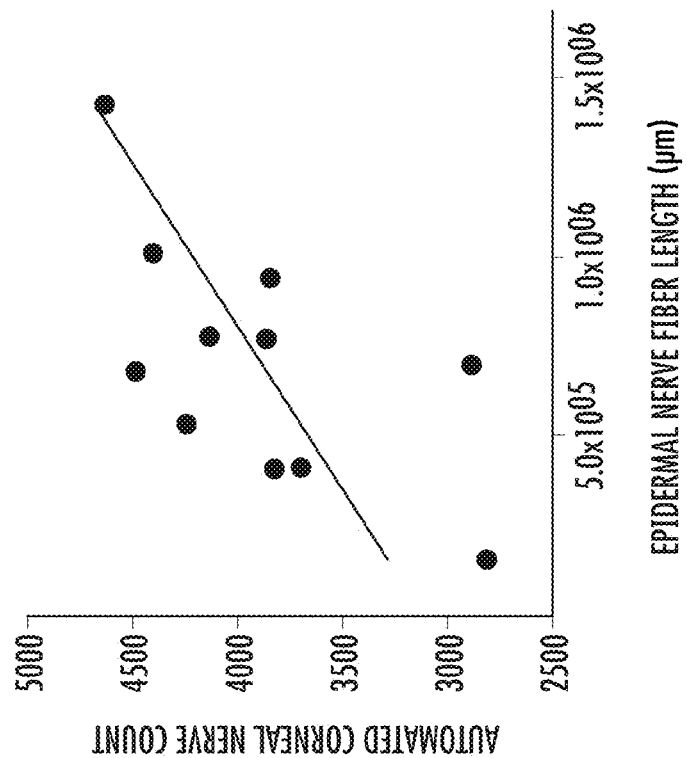
FIGS. 4A and 4B illustrate graphical views of the relationship between ENF length and CNF counts obtained by using either manual or automated corneal counting methods.
Figure 4A:
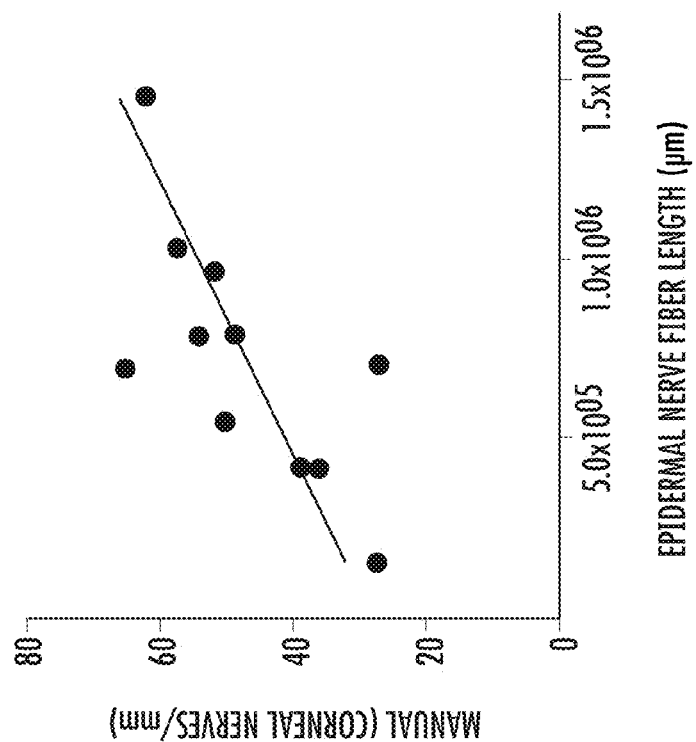

To compare both manual and automated CNF counts with ENF densities, ENF densities were measured in plantar foot punches obtained from SIV-inoculated macaques immunostained for the nerve fiber marker PGP9.5. SIV induces loss of ENF in macaques. Both manual and automated CNF counts were strongly correlated with ENF measurements (P=0.048, r=0.62 for manual counts; P=0.040, r=0.064 for automated counts) (FIGS. 4A and 4B).

Because the cornea is the most densely innervated tissue in the body, corneal nerve assessment is extremely sensitive for detecting damage to small sensory nerve fibers compared with other tests, including measurement of intraepidermal nerve fibers in the skin. The potential for early detection of nerve damage, taken with the rapidity and noninvasiveness of in vivo CCM, has led to increased use of corneal nerve assessments to monitor and evaluate a variety of peripheral neuropathies, particularly diabetic PN. Despite the high prevalence of HIV-PN, as well as the clinical similarities between HIV-PN and diabetic PN, alterations in corneal nerves among persons infected with HIV have not yet been explored. With the use of an SIV/macaque model that closely resembles HIV infection, this study indicated loss of CNFs in the corneal subbasal nerve plexus. Furthermore, CNF counts corresponded closely with measurements of ENF length. CNF loss also was associated with viral replication and cellular immune activation in the trigeminal ganglia, the location of the neuronal cell bodies of the corneal sensory nerve fibers. The relationship between inflammation and SIV replication in the trigeminal ganglia and CNF loss imply that damage to neurons in the trigeminal ganglia impairs the ability of neurons to maintain sensory nerve fiber integrity. Together, these findings indicate that emerging noninvasive techniques to measure CNF alterations such as in vivo CCM may be useful clinical tools to screen for and monitor progression of PN in patients infected with HIV.

Common critiques of current corneal nerve assessments include the requirement for time-intensive manual image analysis and confounding interobserver variability in the recognition of nerve fibers, underscoring the need for trained observers. To overcome these difficulties, the present invention provides a consistent cornea immunostaining and image acquisition protocol. To measure CNFs in the SBP, two rapid, easily applied methods for nerve measurements in the SBP were developed: a manual method that counts all nerve fibers crossing a given transect and an automated method that uses a custom algorithm to identify and count nerve fibers. Although both methods offer viable methods of assessment, the benefit of an automated method includes elimination of interobserver variability, thereby eliminating counting bias and subjectivity.

Both counting methods showed decreased CNF density in the rapid progressor group; the difference between the rapid and slow progressor groups was most pronounced with the use of the automated method of nerve detection. This discrepancy may reflect the method of immunostaining that enhances visibility of all CNFs as well as the differences in the sensitivity of nerve fiber detection between the methods. With the use of the manual method, every nerve fiber is counted regardless of size or thickness to reduce counting subjectivity. In contrast, the automated algorithm is less likely to identify very fine nerve branches, with detection largely limited to the thicker nerve trunks, similar to current in vivo CCM technology wherein many of the very fine nerve fibers also elude detection. The difference in nerve fiber populations identified suggests that the density of thicker nerve trunks may better reflect the severity of CNF damage in SIV.

In this study, to reduce analysis time and to minimize observer variability, density measurements were focused on, a parameter shown to have high intraobserver and interobserver repeatability and agreement. However, other morphological parameters such as fiber length, branch density, and tortuosity of subbasal corneal nerves also have been shown to undergo significant changes throughout progression of PN disease, even when clinical symptoms are mild or absent and skin ENF measurements appear normal. Future studies that use corneal nerve assessment as a surrogate for HIV-PN should also include measurements of these parameters to expand the understanding of CNF damage as well as repair throughout the course of infection. Moreover, the present exemplary implementation was limited to terminal end points of disease because of the immunohistochemical staining method of nerve visualization that necessitated dissected corneal whole mounts. However, the move to noninvasive and thus repeatable methods of nerve detection such as in vivo CCM using the Rostock confocal microscope facilitates study of PN by enabling early detection of damage and progression of nerve fiber deterioration and would enable assessment of therapeutic strategies in the SIV/macaque model. Furthermore, adapting in vivo CCM for use in tracking HIV-induced PNS damage in patients may be of great value in identifying and preventing early PNS damage independent of performing skin biopsies.

A non-transitory computer readable medium that can be read and executed by any computing device can be used for implementation of the present invention. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard disk, reel-to-reel tape, cartridge tape, cassette tapes or cards, optical media such as CD-ROM, DVD, Blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, RFID, or any other suitable data transmission means known to or conceivable by one of skill in the art. A special computing device with imaging capabilities and configured to execute the method of the present invention is also included in the invention.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A non-transitory computer readable medium programmed with steps comprising:
    receiving image data related to a region of interest of the subject;
    dividing the image data into sub-regions, wherein each sub-region is defined by having nerve fibers running in approximately a same direction;
    summing image intensities in the same direction of the nerve fibers for the sub-region;
    reducing a two-dimensional representation to a one-dimensional signal having peaks where the nerve fibers are located; and
    determining a nerve fiber count based on the peaks of the one-dimensional signal.

2. The non-transitory computer readable medium of claim 1, further comprising receiving image data related to a cornea of the subject.

3. The non-transitory computer readable medium of claim 1, further comprising receiving image data from in vivo corneal confocal microscopy.

4. The non-transitory computer readable medium of claim 1, further comprising receiving image data from a whole mount specimen.

5. The non-transitory computer readable medium of claim 4, further comprising the whole mount specimen being stained with βIII tubulin.

6. The non-transitory computer readable medium of claim 1, further comprising comparing the nerve fiber count to a previous nerve fiber count or a normal nerve fiber count to diagnose peripheral neuropathy.

7. The non-transitory computer readable medium of claim 1, further comprising comparing the nerve fiber count to a previous nerve fiber count in order to diagnose onset of or changes in extent of peripheral neuropathy.

8. The non-transitory computer readable medium of claim 1, further comprising receiving in vivo image data from a confocal microscope.

9. The non-transitory computer readable medium of claim 1, further comprising deriving measures of length, tortuosity, branching, and density to diagnose peripheral neuropathy.

10. A system for diagnosing peripheral neuropathy in a subject comprising:
    a confocal microscope configured for obtaining image data of a region of interest of a cornea of the subject;
    a non-transitory computer readable medium programmed for:
    receiving the image data of the region of interest of the cornea of the subject;
    dividing the image data into sub-regions, wherein each sub-region is defined by having nerve fibers running in approximately a same direction;
    summing image intensities in the same direction of the nerve fibers for the sub-region;
    reducing a two-dimensional representation to a one-dimensional signal having peaks where the nerve fibers are located; and
    determining a nerve fiber count based on the peaks of the one-dimensional signal.

11. The system of claim 10, further comprising comparing the nerve fiber count to a previous nerve fiber count or a normal nerve fiber count to diagnose peripheral neuropathy.

12. The system of claim 10, further comprising comparing the nerve fiber count to a previous nerve fiber count in order to diagnose onset of or changes in extent of peripheral neuropathy.

13. The system of claim 10, further comprising receiving in vivo image data from a confocal microscope.

14. The system of claim 10, further comprising deriving measures of length, tortuosity, branching, and density to diagnose peripheral neuropathy.

15. The system of claim 10, further comprising a computing device.

16. The system of claim 10, further comprising the computing device being networked with the confocal microscope in order to receive the image data.

17. The system of claim 10, further comprising a database for storing the image data.

18. The system of claim 17, wherein a computing device is networked with the database for receiving the image data.

19. The system of claim 17, wherein image data stored on the data base is analyzed to determine baseline never counts that indicate peripheral neuropathy.

20. The system of claim 10, further comprising assessing peripheral neuropathy based on the nerve fiber count.

* * * * *